(12) United States Patent
Cullings et al.

(10) Patent No.: US 8,759,057 B1
(45) Date of Patent: Jun. 24, 2014

(54) METHODS FOR PURIFYING ENZYMES FOR MYCOREMEDIATION

(71) Applicant: The United States of America as Represented by the Administrator of the National Aeronautics & Space Administration (NASA), Washington, DC (US)

(72) Inventors: Kenneth W. Cullings, Ventura, CA (US); Julia C. DeSimone, San Jose, CA (US); Chad D. Paavola, Carmel, IN (US)

(73) Assignee: The United States of America as Represented by the Administrator of the National Aeronautics & Space Administration (NASA), Washington, DC (US)

( * ) Notice: Subject to any disclaimer, the term of this patent is extended or adjusted under 35 U.S.C. 154(b) by 0 days.

(21) Appl. No.: 13/854,620

(22) Filed: Apr. 1, 2013

Related U.S. Application Data

(63) Continuation-in-part of application No. 13/438,793, filed on Apr. 3, 2012.

(60) Provisional application No. 61/619,906, filed on Apr. 3, 2012, provisional application No. 61/471,605, filed on Apr. 4, 2011.

(51) Int. Cl.
*C12N 9/98* (2006.01)
*C12N 9/02* (2006.01)
*C12N 9/00* (2006.01)

(52) U.S. Cl.
CPC ............... *C12N 9/00* (2013.01); *C12N 9/0004* (2013.01); *C12N 9/98* (2013.01)
USPC ............................ 435/183; 435/187; 435/189

(58) Field of Classification Search
None
See application file for complete search history.

(56) References Cited

FOREIGN PATENT DOCUMENTS

EP 2078755 A1 * 7/2009 ............... C12P 1/02

OTHER PUBLICATIONS

Wang, H.X. et al. 2006. Purification of a laccase from fruiting bodies of the mushroom *Pleurotus eryngii*. Applied Microbiology and Biotechnology 69:521-525.*

Cullings, et al., Effects of Artificial Defoliation of Pines on the Structure and Physiology of the Soil . . . , Applied and Environmental Microbiology, Apr. 2005, 1996-2000.

Wang, et al., Purification of a laccase from fruiting bodies of the mushroom *Pleurotus eryngii*, App Microbol Biotechnol 2006, 69:521-525.

* cited by examiner

*Primary Examiner* — John S Brusca
*Assistant Examiner* — Sharon M Papciak
(74) *Attorney, Agent, or Firm* — Christopher J. Menke; Robert M. Padilla

(57) ABSTRACT

A process for purifying laccase from an ectomycorrhizal fruiting body is disclosed. The process includes steps of homogenization, sonication, centrifugation, filtration, affinity chromatography, ion exchange chromatography, and gel filtration. Purified laccase can also be separated into isomers.

7 Claims, 1 Drawing Sheet

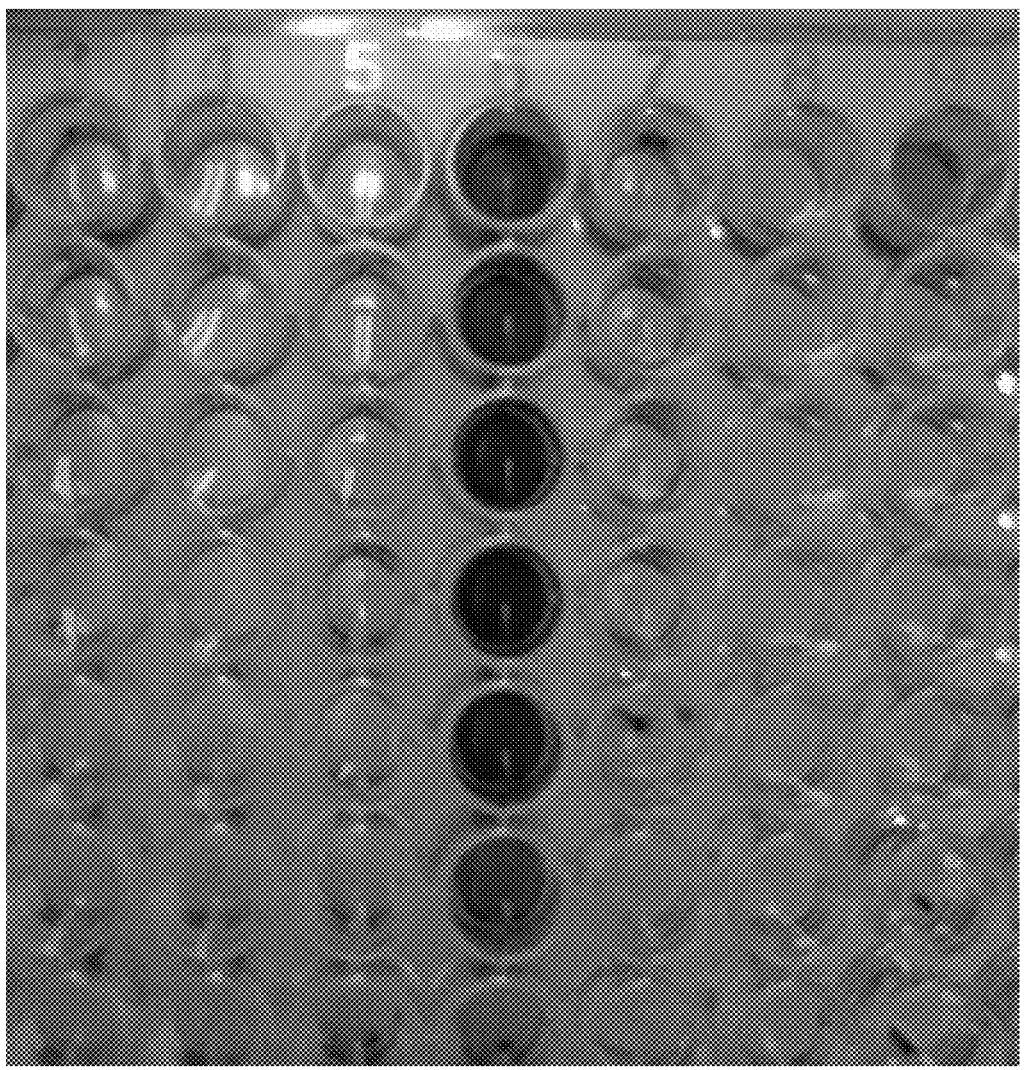

METHODS FOR PURIFYING ENZYMES FOR MYCOREMEDIATION

CROSS-REFERENCE TO RELATED APPLICATIONS

This application claims the benefit of U.S. Provisional Application No. 61/619,906, filed Apr. 3, 2012 and is a continuation-in-part of U.S. application Ser. No. 13/438,793, filed Apr. 3, 2012, which claims the benefit of U.S. Provisional Application No. 61/471,605, filed Apr. 4, 2011, all three of which are incorporated by reference in their entirety herein.

ORIGIN OF THE INVENTION

The invention described herein was made in part by employees of the United States Government and may be manufactured and used by or for the Government of the United States of America for governmental purposes without the payment of any royalties thereon or therefor.

BACKGROUND OF THE INVENTION

This invention relates to bioremediation of contaminants in the environment. More particularly, this invention relates to using fungi to degrade or sequester contaminants in the environment.

Bioremediation is emerging as a cost effective and efficient way to remediate environmental hazards. The work is performed naturally by microbes (bacteria and fungi) that are capable of breaking down the long- and short-chain organic backbones of solvents and fuels such as diesel. Fungi are capable of enhancing the natural process by as much as 10-fold through synergistic action with natural bacteria, and they are also capable of rapid remediation of solvents in their own right.

The fungi that perform this function are wood-rotting and ectomycorrhizal fungi. They naturally possess the enzymes necessary to break down the carbon chains found in many types of contamination. Studies of model white rot fungi (e.g., *Pleurotus ostreatus*) indicate that lignin-degrading fungi will degrade lignin and can reduce hydrocarbon contamination in soils by as much as 40% in as little as one month. Much of the work in these reductions is performed by fungal laccases.

Laccases are polyphenol oxidases that utilize a wide array of phenolic substrates that include lignin in wood and soil humic compounds, polycyclic aromatic hydrocarbons (PAH), and polychlorinated biphenyls (PCB's). PAH and PCB's are widespread soil and water contaminants of human origin that can accumulate via several sources, including diesel spills. Laccases are easily inducible, are involved in lignin beak-down, utilize a broad range of substrates, are often extracellular, and reduce toxicity of these compounds via immobilization to humic substances, thus lowering their bioavailability. Hence, laccases are considered excellent candidates for use in remediation.

In one experiment known in the art, a plot of soil contaminated with diesel was inoculated with mycelia of oyster mushrooms; traditional bioremediation techniques (i.e., inoculation with bacteria) were used on control plots. After about a month, much of the polycyclic aromatic hydrocarbons (PAH) had reportedly been reduced to non-toxic components in the mycelia-inoculated plots. It appears the natural microbial community participates with the fungi to break down contaminants, eventually into carbon dioxide and water. Also known in the art, white-rot or wood-decay fungi have been found to be effective in breaking down aromatic pollutants (toxic components of petroleum), as well as chlorinated compounds (certain persistent pesticides).

H. X. Wang & T. B. Ng, Purification of a laccase from fruiting bodies of the mushroom *Pleurotus eryngii*, 69 Appl. Microbiol. Biotechnol. 521-525 (2006), describes a basic laccase purification method for the mushroom, *Pleurotus eryngii*. The disclosed method is insufficient for use in purifying laccases from fungi that contain more fleshy structures and fails to provide for separation of laccase isozymes. Therefore, an improved, broadened, and expanded method that would apply to many more types of fungi is needed.

While prior art methods of laccase purification are known and are generally suitable for their limited purposes, they possess certain inherent deficiencies that detract from their overall utility in environmental bioremediation. For example, they are not generally applicable to mushroom-forming fungi. They are generally suitable for use with some fruiting bodies, but they are not well suited for use with fleshier fungal species. As a further example, they do not provide for separation of enzyme isomers and purification of such isomers.

Bio-prospectors continue to search for new forms of mycoremediation and new methods of decontaminating the environment because prior art products and methods, though generally suitable for their limited purposes, possess certain inherent deficiencies that detract from their overall utility in environmental bioremediation.

In view of the foregoing, it will be appreciated that providing improved products and methods for environmental bioremediation would be a significant advancement in the art.

SUMMARY OF THE INVENTION

An illustrative embodiment of a process according to the present invention for purifying laccase from an ectomycorrhizal fruiting body comprises:

(A) homogenizing the fruiting body in a buffer of about pH 7 to obtain a slurry;

(B) sonicating the slurry to obtain a sonicated slurry;

(C) centrifuging the sonicated slurry at a relative centrifugal force of about 15,000 to about 20,000 and collecting a resulting first supernatant;

(D) sonicating the first supernatant to obtain a sonicated first supernatant;

(E) ultracentrifuging the sonicated first supernatant such that a resulting second supernatant separates into top and bottom supernatant layers, and collecting the bottom supernatant layer;

(F) filtering the bottom supernatant layer through a bacteria-retaining filter and collecting the filtrate;

(G) subjecting the filtrate to DEAE cellulose chromatography and eluting retained proteins with a first sodium chloride gradient;

(H) removing the sodium chloride from the eluted, retained proteins to obtain desalted proteins, subjecting the desalted proteins to ion exchange chromatography, desorbing adsorbed proteins with a second sodium chloride gradient, and collecting the first desorbed peak; and (I) fractionating the first desorbed peak into fractions by gel filtration.

BRIEF DESCRIPTION OF THE DRAWING

FIG. 1 shows enzymatic activity of a laccase purified according to an illustrative embodiment of the present invention (column 6); a positive control is shown in column 9.

DETAILED DESCRIPTION OF THE INVENTION

Before the processes of the presently claimed invention are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a laccase" includes reference to a mixture of two or more laccases, reference to "an ectomycorrhizal fruiting body" includes reference to one or more of such fruiting bodies, and reference to "the product" includes reference to a mixture of two or more of such products.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As mentioned above, illustrative embodiments of the present invention include processes for purifying laccase from ectomycorrhizal fruiting bodies and processes for separating purified laccase into isomers. These processes will be further described in the examples that follow. The scope of the invention, however, will be limited only by the claims.

Example 1

Prior Art

H. X. Wang & T. B. Ng, Purification of a laccase from fruiting bodies of the mushroom *Pleurotus eryngii*, 69 Appl. Microbiol. Biotechnol. 521-525 (2006), describes the purification of laccase as follows:

The fruiting bodies of *Pleurotus eryngii* (2 kg) were extracted by homogenization in distilled water (2 ml/g). The homogenate was filtered through cheesecloth before centrifugation. The resulting supernatant was applied to a 5×20 cm diethylaminoethyl (DEAE) cellulose (Sigma) column in 10 mM Tris HCl buffer (ph 7.3). Following removal of unadsorbed proteins, the column was eluted with 0.8 M NaCl added to the Tris HCl buffer. The adsorbed fraction was dialyzed prior to loading on a 2.5×20 cm column of carboxymethyl (CM) cellulose (Sigma) in 10 mM NH4OAc buffer (ph 5.1). After removal of unadsorbed proteins, adsorbed proteins were desorbed by addition of 1 M NaCl to the elution buffer. The unadsorbed fraction was subsequently subjected to ion exchange chromatography on a 1.5×20 cm Q-SEPHAROSE® column (Amersham Biosciences) in 10 mM NH4OAc buffer (ph 5.1). Unadsorbed proteins were eluted with the same buffer. Adsorbed proteins were desorbed with a linear 0-1 M NaCl gradient in 10 mM NH4OAc buffer (ph 5.1). The first adsorbed peak obtained was fractionated by gel filtration on a SUPERDEX® 75 HR 10/30 column (Amersham Biosciences) by fast protein liquid chromatography (FPLC).

Example 2

Improved Laccase Purification

The method of Example 1 was carried out, with the following changes. Fruiting bodies of *Suilllus granulatus* were homogenized in 10 mM Tris-HCl buffer, pH 7.3, instead of in water. Filtration through cheesecloth was omitted, because the homogenate was too thick to pass readily through the cheesecloth filter. Instead, the slurry was sonicated, then centrifuged at 10,500 rpm (relative centrifugal force (RCF) of 18,093). The supernatant was collected, sonicated, and ultracentrifuged at 45,000 rpm. This treatment caused the supernatant to separate into two layers. The bottom supernatant layer was collected and then filtered using a 0.45 Fm syringe filter (polyethersulfone, PES). The filtrate was loaded onto a DEAE Sepharose column and eluted using an NaCl gradient. Dialysis was performed on the active fractions as described in Example 1. The CM cellulose chromatography step was omitted, but the ion exchange chromatography on Q-SEPHAROSE® and gel filtration on SUPERDEX® 75 were carried out as described in Example 1.

Example 3

Laccase purified according to the procedure of Example 2 was separated into isomers as follows. Active fractions were concentrated to <2 ml using a VivaSpin centrifugal filter (PES; 10,000 MWCO), and assayed for concentration and specific activity, then loaded onto a Phenyl Fast-Flow (low substitution) HIC (hydrophobic interaction chromatography) column. This treatment resulted in five peaks, the most active being of interest. Active fractions after HIC chromatography were concentrated to <1 ml using a VivaSpin (Vivaproducts, Inc., Littleton, Mass.) centrifugal filter (PES; 10,000 MWCO), and assayed for concentration and specific activity, resulting in separation and the obtaining of pure individual enzyme.

Example 4

Laccase purified according to the procedure of Example 2 was assayed for phenol oxidation activity in an ABTS (2,2'-azino-bis(3-ethylbenzothiazoline-6-sulfonic acid) assay according to procedures well known in the art. The sample to be assayed was placed in 100 mM sodium tartrate buffer (pH 4.3) containing ABTS. The increase in absorbance at 405 nm was recorded over 15 min.

FIG. 1 shows the results of such an assay. Laccase purified from a *Russula* species is shown in the wells in column 6. *Trametes versicolor* laccase purchased from Sigma Chemical Co. (St. Louis, Mo.) was a positive control, as shown in column 9.

These results demonstrate that laccase purified according to the present invention contains phenol oxidation activity, which is consistent with known laccase enzymes.

What is claimed is:

1. A process for purifying laccase from an ectomycorrhizal fruiting body, the process comprising:
   (A) homogenizing the fruiting body in a buffer of about pH 7 to obtain a slurry;
   (B) sonicating the slurry to obtain a sonicated slurry;
   (C) centrifuging the sonicated slurry at a relative centrifugal force of about 15,000 to about 20,000 and collecting a resulting first supernatant;
   (D) sonicating the first supernatant to obtain a sonicated first supernatant;
   (E) ultracentrifuging the sonicated first supernatant such that a resulting second supernatant separates into top and bottom supernatant layers, and collecting the bottom supernatant layer;
   (F) filtering the bottom supernatant layer through a bacteria-retaining filter and collecting the filtrate;
   (G) subjecting the filtrate to DEAE cellulose chromatography and eluting retained proteins with a first sodium chloride gradient;
   (H) removing the sodium chloride from the eluted, retained proteins to obtain desalted proteins, subjecting the desalted proteins to ion exchange chromatography, desorbing adsorbed proteins with a second sodium chloride gradient, and collecting the first desorbed peak; and
   (I) fractionating the first desorbed peak into fractions by gel filtration.

2. The process of claim 1, wherein the ultracentrifuging is at about 45,000 rpm.

3. The process of claim 1, wherein the ion exchange chromatography of step (H) is carried out on a column.

4. The process of claim 1, wherein the gel filtration of step (I) is carried out on a column by fast protein liquid chromatography.

5. The process of claim 1, further comprising assaying the fractions of step (I) for phenol oxidation activity.

6. The process of claim 5, wherein phenol oxidation activity is assayed by (2,2'-azino-bis(3-ethylbenzothiazoline-6-sulfonic acid) ("ABTS") assay.

7. The process of claim 1, further comprising separating fractions from the gel filtration step of step (I) into laccase isomers by hydrophobic interaction chromatography.

* * * * *